United States Patent
Rawlins et al.

(10) Patent No.: US 7,423,043 B2
(45) Date of Patent: Sep. 9, 2008

(54) 4-PIPERIDIN-1-YL-7H-PYRROLO[2,3-D] PYRIMIDINE COMPOUNDS

(75) Inventors: David Brent Rawlins, Morrisville, PA (US); Michael Victor Voronkov, Pennington, NJ (US); Yulian Zhang, Yardley, PA (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 256 days.

(21) Appl. No.: 11/354,636

(22) Filed: Feb. 15, 2006

(65) Prior Publication Data

US 2006/0189638 A1    Aug. 24, 2006

Related U.S. Application Data

(60) Provisional application No. 60/675,254, filed on Apr. 27, 2005, provisional application No. 60/654,107, filed on Feb. 18, 2005.

(51) Int. Cl.
  C07D 487/04   (2006.01)
  A61K 31/519  (2006.01)
  A61P 35/04   (2006.01)

(52) U.S. Cl. .................................. 514/265.1; 544/280

(58) Field of Classification Search ................. 544/280; 514/265.1
See application file for complete search history.

(56) References Cited

U.S. PATENT DOCUMENTS

| 6,627,754 B2 | 9/2003 | Blumenkopf et al. |
| 6,635,762 B1 | 10/2003 | Blumenkopf et al. |
| 2004/0058922 A1 | 3/2004 | Blumenkopf et al. |

FOREIGN PATENT DOCUMENTS

| WO | WO 96/40142 A1 | 12/1996 |
| WO | WO 97/27199 A1 | 7/1997 |
| WO | WO 98/23613 A1 | 6/1998 |
| WO | WO 99/65909 A1 | 12/1999 |
| WO | WO 03/002214 A2 | 3/2003 |

OTHER PUBLICATIONS

Pudlo et al., 1988, "Synthesis and Antiviral Activity of Certain 4- and 4,5-Disubstituted 7-[2-Hydroxyethoxy)methyl]pyrrolo[2,3-d]pyrimidnes", J. Med. Chem. 31:2086-2092.

*Primary Examiner*—Brenda Coleman
*Assistant Examiner*—Susanna Moore
(74) *Attorney, Agent, or Firm*—Max Bachrach

(57) ABSTRACT

Substituted 4-piperidin-1-yl-7H-pyrrolo[2,3-D]pyrimidine compounds are disclosed, as well as compositions comprising them and methods of their use for the treatment, prevention and management of various diseases and disorders.

18 Claims, No Drawings

4-PIPERIDIN-1-YL-7H-PYRROLO[2,3-D] PYRIMIDINE COMPOUNDS

This application claims priority to U.S. provisional application Nos. 60/654,107, filed Feb. 18, 2005, and 60/675,254, filed Apr. 27, 2005, both of which are incorporated herein by reference.

1. FIELD OF THE INVENTION

This invention is directed to substituted 4-piperidin-1-yl-7H-pyrrolo[2,3-d]pyrimidine compounds, compositions comprising them, and methods of their use for the treatment, prevention and management of various diseases and disorders.

2. BACKGROUND

It is estimated that 9.8 million Americans with a history of cancer were alive in 2001. American Cancer Society, *Cancer Facts and Figures* 2005, 1. Over one million new cases of cancer are expected to be diagnosed in the United States during 2005, and over 500,000 Americans are expected to die of cancer during that same year. Id. Consequently a great need exists for new drugs that can be used for the safe and effective treatment of cancer.

3. SUMMARY OF THE INVENTION

This invention is directed, in part, to compounds of formula I:

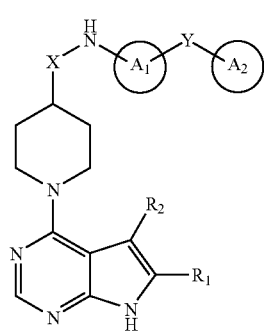

(I)

and pharmaceutically acceptable salts and solvates thereof, wherein:

$A_1$ and $A_2$ are each independently optionally substituted aryl or heteroaryl;

X is —$CH_2$— or —C(O)—;

Y is —O—, —$NR_5$—, —$S(O)_n NR_5$—, —$C(O)NR_5$—, —$NR_5 C(O)$—, —C(O)—, or —$S(O)_n$—;

n is 1 or 2;

$R_1$ and $R_2$ are each independently hydrogen, halo, cyano, hydroxy, —$NR_3 R_4$, thio, or optionally substituted alkyl, alkoxy, aryl, arylalkyl, heterocycle or heterocycloalkylalkyl; and $R_3$, $R_4$, and $R_5$ are each independently hydrogen or optionally substituted alkyl, aryl, arylalkyl, heterocycle or heterocycloalkylalkyl.

This invention also encompasses compositions (e.g., pharmaceutical compositions) comprising compounds of formula I or pharmaceutically acceptable salts or solvates thereof.

This invention also encompasses methods of treating, managing, and preventing various diseases and disorders, which comprise administering to a patient in need thereof a compound of formula I or a pharmaceutically acceptable salt or solvate thereof.

4. DETAILED DESCRIPTION

This invention is based, in part, on the discovery of novel kinase inhibitors, which are capable of disrupting the cell cycle. Compounds of the invention may be useful in the treatment, management or prevention of various disease and disorders, including proliferative diseases such as cancer, cancer metastasis, inflammation, arthritis, and diseases characterized by abnormal or inappropriate angiogenesis.

4.1. Definitions

Unless otherwise indicated, the term "alkenyl" means a straight chain, branched and/or cyclic hydrocarbon having from 2 to 20 (e.g., 2 to 10 or 2 to 6) carbon atoms, and including at least one carbon-carbon double bond. Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

Unless otherwise indicated, the term "alkyl" means a straight chain, branched and/or cyclic ("cycloalkyl") hydrocarbon having from 1 to 20 (e.g., 1 to 10 or 1 to 4) carbon atoms. Alkyl moieties having from 1 to 4 carbons are referred to as "lower alkyl." Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes saturated hydrocarbons as well as alkenyl and alkynyl moieties.

Unless otherwise indicated, the term "alkylaryl" or "alkyl-aryl" means an alkyl moiety bound to an aryl moiety.

Unless otherwise indicated, the term "alkylheteroaryl" or "alkyl-heteroaryl" means an alkyl moiety bound to a heteroaryl moiety.

Unless otherwise indicated, the term "alkylheterocycle" or "alkyl-heterocycle" means an alkyl moiety bound to a heterocycle moiety.

Unless otherwise indicated, the term "alkynyl" means a straight chain, branched or cyclic hydrocarbon having from 2 to 20 (e.g., 2 to 20 or 2 to 6) carbon atoms, and including at least one carbon-carbon triple bond. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

Unless otherwise indicated, the term "alkoxy" means an —O-alkyl group. Examples of alkoxy groups include, but are not limited to, —$OCH_3$, —$OCH_2CH_3$, —$O(CH_2)_2CH_3$, —$O(CH_2)_3CH_3$, —$O(CH_2)_4CH_3$, and —$O(CH_2)_5CH_3$.

Unless otherwise indicated, the term "aryl" means an aromatic ring or an aromatic or partially aromatic ring system composed of carbon and hydrogen atoms. An aryl moiety may comprise multiple rings bound or fused together. Examples of aryl moieties include, but are not limited to, anthracenyl, azulenyl, biphenyl, fluorenyl, indan, indenyl, naphthyl, phenanthrenyl, phenyl, 1,2,3,4-tetrahydro-naphthalene, and tolyl.

Unless otherwise indicated, the term "arylalkyl" or "arylalkyl" means an aryl moiety bound to an alkyl moiety.

Unless otherwise indicated, the terms "halogen" and "halo" encompass fluorine, chlorine, bromine, and iodine.

Unless otherwise indicated, the term "heteroalkyl" refers to an alkyl moiety in which at least one of its carbon atoms has been replaced with a heteroatom (e.g., N, O or S).

Unless otherwise indicated, the term "heteroaryl" means an aryl moiety wherein at least one of its carbon atoms has been replaced with a heteroatom (e.g., N, O or S). Examples include, but are not limited to, acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

Unless otherwise indicated, the term "heteroarylalkyl" or "heteroaryl-alkyl" means a heteroaryl moiety bound to an alkyl moeity.

Unless otherwise indicated, the term "heterocycle" refers to an aromatic, partially aromatic or non-aromatic monocyclic or polycyclic ring or ring system comprised of carbon, hydrogen and at least one heteroatom (e.g., N, O or S). A heterocycle may comprise multiple (i.e., two or more) rings fused or bound together. Heterocycles include heteroaryls. Examples include, but are not limited to, benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl.

Unless otherwise indicated, the term "heterocyclealkyl" or "heterocycle-alkyl" refers to a heterocycle moiety bound to an alkyl moiety.

Unless otherwise indicated, the term "heterocycloalkyl" refers to a non-aromatic heterocycle.

Unless otherwise indicated, the term "heterocycloalkylalkyl" or "heterocycloalkyl-alkyl" refers to a heterocycloalkyl moiety bound to an alkyl moeity.

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

Unless otherwise indicated, the term "pharmaceutically acceptable salts" refers to salts prepared from pharmaceutically acceptable non-toxic acids or bases including inorganic acids and bases and organic acids and bases. Suitable pharmaceutically acceptable base addition salts include, but are not limited to, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine(N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art. See, e.g., *Remington's Pharmaceutical Sciences* (18th ed., Mack Publishing, Easton Pa.: 1990) and *Remington: The Science and Practice of Pharmacy* (19th ed., Mack Publishing, Easton Pa.: 1995).

Unless otherwise indicated, the terms "prevent," "preventing" and "prevention" contemplate an action that occurs before a patient begins to suffer from the specified disease or disorder, which inhibits or reduces the severity of the disease or disorder. In other words, the terms encompass prophylaxis.

Unless otherwise indicated, a "prophylactically effective amount" of a compound is an amount sufficient to prevent a disease or condition, or one or more symptoms associated with the disease or condition, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Unless otherwise indicated, the term "stereoisomeric mixture" encompasses racemic mixtures as well as stereomerically enriched mixtures (e.g., R/S=30/70, 35/65, 40/60, 45/55, 55/45, 60/40, 65/35 and 70/30).

Unless otherwise indicated, the term "stereomerically pure" means a composition that comprises one stereoisomer of a compound and is substantially free of other stereoisomers of that compound. For example, a stereomerically pure composition of a compound having one stereocenter will be substantially free of the opposite stereoisomer of the compound. A stereomerically pure composition of a compound having two stereocenters will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

Unless otherwise indicated, the term "substituted," when used to describe a chemical structure or moiety, refers to a derivative of that structure or moiety wherein one or more of its hydrogen atoms is substituted with a chemical moiety or functional group such as, but not limited to, alcohol, aldehylde, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkyl-NHC(O)alkyl), amidinyl (—C(NH)NH-alkyl or —C(NR)

$NH_2$), amine (primary, secondary and tertiary such as alkylamino, arylamino, arylalkylamino), aroyl, aryl, aryloxy, azo, carbamoyl (—NHC(O)O-alkyl- or —OC(O)NH-alkyl), carbamyl (e.g., $CONH_2$, as well as CONH-alkyl, CONH-aryl, and CONH-arylalkyl), carbonyl, carboxyl, carboxylic acid, carboxylic acid anhydride, carboxylic acid chloride, cyano, ester, epoxide, ether (e.g., methoxy, ethoxy), guanidino, halo, haloalkyl (e.g., —$CCl_3$, —$CF_3$, —$C(CF_3)_3$), heteroalkyl, hemiacetal, imine (primary and secondary), isocyanate, isothiocyanate, ketone, nitrile, nitro, oxo, phosphodiester, sulfide, sulfonamido (e.g., $SO_2NH_2$), sulfone, sulfonyl (including alkylsulfonyl, arylsulfonyl and arylalkylsulfonyl), sulfoxide, thiol (e.g., sulfhydryl, thioether) and urea (—NHCONH-alkyl-).

Unless otherwise indicated, a "therapeutically effective amount" of a compound is an amount sufficient to provide a therapeutic benefit in the treatment or management of a disease or condition, or to delay or minimize one or more symptoms associated with the disease or condition. A therapeutically effective amount of a compound means an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder, or retards or slows the progression of the disease or disorder.

Unless otherwise indicated, the term "include" has the same meaning as "include, but are not limited to," and the term "includes" has the same meaning as "includes, but is not limited to." Similarly, the term "such as" has the same meaning as the term "such as, but not limited to."

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

It should be noted that a chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, the two phrases "XOH, wherein X is pyridyl" and "XOH, wherein X is pyridine" are accorded the same meaning, and encompass the compounds pyridin-2-ol, pyridin-3-ol and pyridin-4-ol.

It should also be noted that if the stereochemistry of a structure or a portion of a structure is not indicated with, for example, bold or dashed lines, the structure or the portion of the structure is to be interpreted as encompassing all stereoisomers of it. Moreover, any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit.

4.2. Compounds

Compounds of the invention include compounds of formula I:

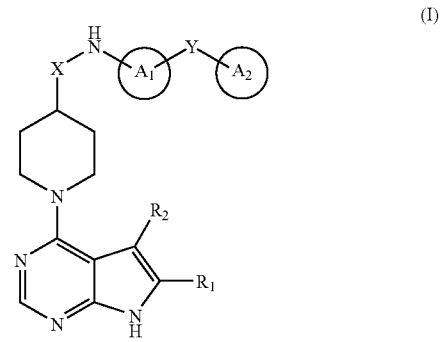

(I)

and pharmaceutically acceptable salts and solvates thereof, wherein:

$A_1$ and $A_2$ are each independently optionally substituted aryl or heteroaryl;

X is —$CH_2$— or —C(O)—;

Y is —O—, —$NR_5$—, —$S(O)_nNR_5$—, —$C(O)NR_5$—, —$NR_5C(O)$—, —C(O)—, or —$S(O)_n$—;

n is 1 or 2;

$R_1$ and $R_2$ are each independently hydrogen, halo, cyano, hydroxy, —$NR_3R_4$, thio, or optionally substituted alkyl, alkoxy, aryl, arylalkyl, heterocycle or heterocycloalkylalkyl; and $R_3$, $R_4$, and $R_5$ are each independently hydrogen or optionally substituted alkyl, aryl, arylalkyl, heterocycle or heterocycloalkylalkyl.

In one embodiment, $R_1$ and $R_2$ are each independently hydrogen, alkyl, halo or cyano.

In another embodiment, $A_1$ is aryl.

In another embodiment, $A_2$ is aryl or heteroaryl.

In another embodiment, X is —C(O)—.

In another embodiment, Y is —O—.

In a specific embodiment, $R_1$ and $R_2$ are each independently hydrogen, alkyl, halo, or cyano; $A_1$ is aryl; $A_2$ is aryl or heteroaryl; X is —$CH_2$—; and Y is —O—.

Another embodiment of the invention encompasses compounds of formula II:

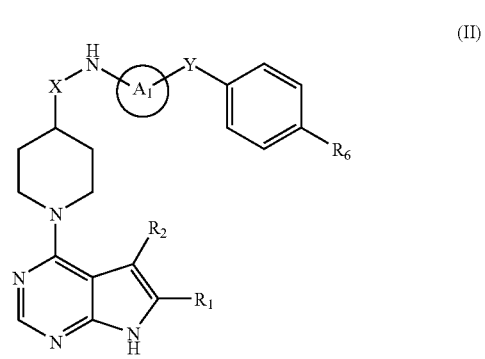

(II)

and pharmaceutically acceptable salts and solvates thereof, wherein:

$A_1$ is optionally substituted aryl or heteroaryl;

X is —$CH_2$— or —C(O)—;

Y is —O—, —$NR_5$—, —$S(O)_nNR_5$—, —$C(O)NR_5$—, —$NR_5C(O)$—, —C(O)—, or —$S(O)_n$—;

n is 1 or 2;

$R_1$ and $R_2$ are each independently hydrogen, halo, cyano, hydroxy, —$NR_3R_4$, thio, or optionally substituted alkyl, alkoxy, aryl, arylalkyl, heterocycle or heterocycloalkylalkyl; and $R_3$, $R_4$, and $R_5$ are each independently hydrogen or optionally substituted alkyl, aryl, arylalkyl, heterocycle or heterocycloalkylalkyl; and $R_6$ is hydrogen, halo, cyano, hydroxy, alkoxy, amino or optionally substituted alkyl.

In one embodiment, $A_1$ is thiazol or optionally substituted phenyl.

In another embodiment, Y is —O— or —NHC(O)—.

In another embodiment, n is 2.

In another embodiment, $R_1$ is hydrogen.

In another embodiment, $R_2$ is hydrogen, methyl or halo.

In another embodiment, $R_3$ is hydrogen or alkyl.

In another embodiment, $R_4$ is hydrogen or alkyl.

In another embodiment, $R_5$ is hydrogen or alkyl.

In another embodiment, $R_6$ is halo.

Another embodiment of the invention encompasses compounds of formula III:

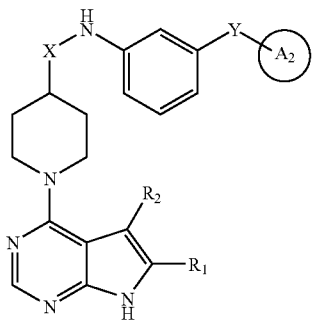

(III)

and pharmaceutically acceptable salts and solvates thereof, wherein:

$A_2$ is optionally substituted aryl or heteroaryl;

X is —$CH_2$— or —C(O)—;

Y is —O—, —$NR_5$—, —$S(O)_nNR_5$—, —$C(O)NR_5$—, —$NR_5C(O)$—, —C(O)—, or —$S(O)_n$—;

n is 1 or 2;

$R_1$ and $R_2$ are each independently hydrogen, halo, cyano, hydroxy, —$NR_3R_4$, thio, or optionally substituted alkyl, alkoxy, aryl, arylalkyl, heterocycle or heterocycloalkylalkyl; and $R_3$, $R_4$, and $R_5$ are each independently hydrogen or optionally substituted alkyl, aryl, arylalkyl, heterocycle or heterocycloalkylalkyl.

In one embodiment, $A_2$ is optionally substituted phenyl, indanyl, indenyl, indolinyl, or pyridyl.

In another embodiment, Y is —O— or —NHC(O)—.

In another embodiment, n is 2.

In another embodiment, $R_1$ is hydrogen.

In another embodiment, $R_2$ is hydrogen, methyl or halo.

In another embodiment, $R_3$ is hydrogen or alkyl.

In another embodiment, $R_4$ is hydrogen or alkyl.

In another embodiment, $R_5$ is hydrogen or alkyl.

In another embodiment, $R_6$ is halo.

All stereoisomers of the compounds disclosed herein are contemplated, either in admixture or in pure or substantially pure form. For example, formula I embraces all possible stereoisomers and their mixtures, including racemic forms and the isolated optical isomers having specified activity. Thus, this invention encompasses stereomerically pure forms of the compounds disclosed herein, which can be prepared by stereoselective synthetic methods or isolated from racemic or diasteromeric mixtures by methods known in the art such as, for example, fractional crystallization, separation or crystallization of diastereomeric derivatives or separation by chiral column chromatography, and chiral salt formation.

This invention further encompasses stereoisomeric mixtures of compounds disclosed herein. It also encompasses configurational isomers of compounds disclosed herein, either in admixture or in pure or substantially pure form, such as cis (Z) and trans (E) alkene isomers.

4.3. Synthesis

The synthesis of compounds of formula I can proceed through the known 4-chloro-5-methyl-7H-pyrrolo[2,3-d]pyrimidine of formula 1, which can be prepared according to the procedures set forth in *J. Org. Chem.* 26:4959 (1961) and the references therein, as depicted in Scheme 1, below.

Scheme 1

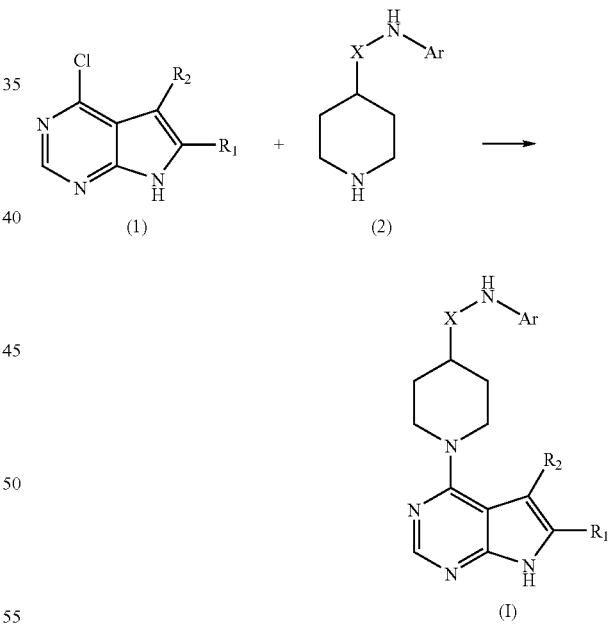

In this approach, a compound of formula 1 is contacted with a compound of formula 2 under reaction conditions sufficient for provide a compound of formula I. For example, this can occur in the presence of an amine (e.g., triethylamine) in an alcoholic solvent (e.g., isopropyl alcohol) at reflux.

Compounds of the invention may also be synthesized by reacting compounds of formula 1 with piperidinyl esters such as compounds of formula 3 to give compounds of formula 4, as shown in Scheme 2, below.

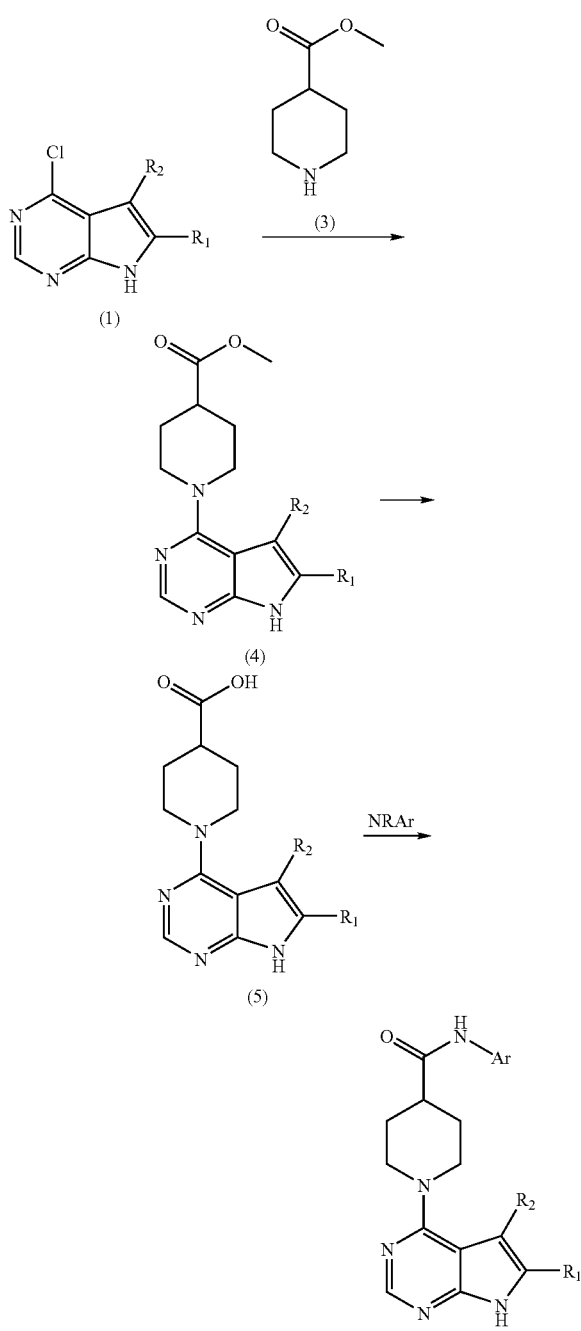

The esters can then be hydrolyzed using agents such as aqueous lithium hydroxide to give acids of formula 5. The acids of formula 5 can then be coupled to amines under standard conditions to provide the desired compound of the invention.

4.4. Methods of Use

This invention is based, in part, on the discovery of compounds that can act as kinase inhibitors. The compounds are believed to be useful in the treatment, prevention and/or management of a variety of diseases and disorders such as proliferative diseases (e.g., cancer), inflammatory diseases, and diseases characterized by abnormal or inappropriate anglogenesis.

This invention encompasses methods of treating diseases and disorders which comprise administering a therapeutically effective amount of a compound disclosed herein to a patient (e.g., a mammal, preferably a human) in need thereof. In some cases, a compound of the invention is administered in combination with one or more additional active agents. An additional active agent may be administered to provide relief from adverse effects (e.g., nausea, headache), or to provide additive or synergistic therapeutic or prophylactic effect.

This invention also encompasses methods of managing diseases and disorders which comprise administering a prophylactically effective amount of a compound disclosed herein to a patient in need thereof.

This invention also encompasses methods of preventing diseases and disorders which comprise administering a prophylactically effective amount of a compound disclosed herein to a patient in need thereof.

One embodiment of the invention encompasses a method of treating, managing or preventing cancer. Cancers can be solid or blood-borne. Examples of cancer include, but are not limited to, cancers of the skin, such as melanoma; lymph node; breast; cervix; uterus; gastrointestinal tract; lung; ovary; prostate; colon; rectum; mouth; brain; head and neck; throat; testes; kidney; pancreas; bone; spleen; liver; bladder; larynx; nasal passages; and AIDS-related cancers.

4.5. Pharmaceutical Compositions

This invention encompasses pharmaceutical compositions comprising one or more compounds of the invention. Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the compounds of this invention from degradation within the gastrointestinal tract. Similarly, a formulation may contain ingredients that facilitate delivery of the active ingredient(s) to the site of action. For example, compounds may be administered in liposomal formulations, in order to protect them from degradative enzymes, facilitate transport in circulatory system, and effect delivery across cell membranes to intracellular sites.

Similarly, poorly soluble compounds may be incorporated into liquid dosage forms (and dosage forms suitable for reconstitution) with the aid of solubilizing agents, emulsifiers and surfactants such as, but not limited to, cyclodextrins (e.g., α-cyclodextrin, β-cyclodextrin, Captisol®, and Encapsin™ (see generally Davis and Brewster, 2004, *Nat. Rev. Drug Disc.* 3:1023-1034), Labrasol®, Labrafil®, Labrafac®, cremafor, and non-aqueous solvents, such as, but not limited to, ethyl alcohol, isopropyl alcohol, ethyl carbonate, ethyl acetate, benzyl alcohol, benzyl benzoate, propylene glycol, 1,3-butylene glycol, dimethyl formamide, dimethyl sulfoxide (DMSO), biocompatible oils (e.g., cottonseed, groundnut, corn, germ, olive, castor, and sesame oils), glycerol, tetrahydrofurfuryl alcohol, polyethylene glycols, fatty acid esters of sorbitan, and mixtures thereof (e.g., DMSO:comoil).

Poorly soluble compounds may also be incorporated into suspensions using other techniques known in the art. For example, nanoparticles of a compound may be suspended in a liquid to provide a nanosuspension (see, e.g., Rabinow, 2004, *Nature Rev. Drug Disc.* 3:785-796). Nanoparticle forms of compounds described herein may be prepared by the methods described in U.S. Patent Publication Nos. 2004-0164194, 2004-0195413, 2004-0251332, 2005-0042177 A1, 2005-0031691 A1, and U.S. Pat. Nos. 5,145,684, 5,510,118, 5,518,187, 5,534,270, 5,543,133, 5,662,883, 5,665,331, 5,718,388, 5,718,919, 5,834,025, 5,862,999, 6,431,478, 6,742,734, 6,745,962, the entireties of each of which are incorporated herein by reference. In one embodiment, the nanoparticle form comprises particles having an average particle size of less than about 2000 nm, less than about 1000 nm, or less than about 500 nm.

The composition, shape, and type of a dosage form will vary depending on its use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990).

4.5.1. Oral Dosage Forms

Pharmaceutical compositions of the invention suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms are prepared by combining the active ingredient(s) in an intimate admixture with at least one excipient according to conventional pharmaceutical compounding techniques. Excipients can take a wide variety of forms depending on the form of preparation desired for administration.

Because of their ease of administration, tablets and capsules represent the most advantageous oral dosage unit forms. If desired, tablets can be coated by standard aqueous or non-aqueous techniques. Such dosage forms can be prepared by conventional methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. Disintegrants may be incorporated in solid dosage forms to facility rapid dissolution. Lubricants may also be incorporated to facilitate the manufacture of dosage forms (e.g., tablets).

4.5.2. Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are specifically sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

4.5.3. Transdermal, Topical and Mucosal Dosage Forms

Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences,* 16th and 18th eds., Mack Publishing, Easton Pa. (1980 & 1990); and *Introduction to Pharmaceutical Dosage Forms,* 4th ed., Lea & Febiger, Philadelphia (1985). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms are well known to those skilled in the pharmaceutical arts, and depend on the particular tissue to which a given pharmaceutical composition or dosage form will be applied.

Depending on the specific tissue to be treated, additional components may be used prior to, in conjunction with, or subsequent to treatment with active ingredients of the invention. For example, penetration enhancers may be used to assist in delivering active ingredients to the tissue.

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates may also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

4.5.4. Delayed and Extended Release Dosage Forms

Compounds of the invention may be administered by controlled release (e.g., delayed release and extended release) means known in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multi layer coatings, microparticles, liposomes, microspheres, or a combination thereof to provide the desired release profile in varying proportions. Suitable controlled-release formulations known to those of ordinary skill in the art, including those described herein, can be readily selected for use with the compounds of this invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.5.5. Kits

This invention encompasses kits which can simplify the administration of one or more active ingredients to a patient. A typical kit comprises single unit dosage form(s) of one or more active ingredients (e.g., a compound of the invention), in addition to one or more devices that may be used to administer the active ingredient(s). Examples of such devices include, but are not limited to, syringes, drip bags, patches, and inhalers.

Kits can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

4.5.6. Compositions with Enhanced Stability

The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, this invention encompasses pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions of the invention can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are specifically anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are specifically packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients.

5. EXAMPLES

The following are examples of certain embodiments of the invention, and should not be interpreted as limiting the scope of the invention in any way.

5.1. Preparation of 1-(5-Methyl-7H-pyrrolo[2,3-d]pyrimidin-4-yl)-piperidine-4-carboxylic acid [3-(4-fluoro-phenoxy)-phenyl]-amide

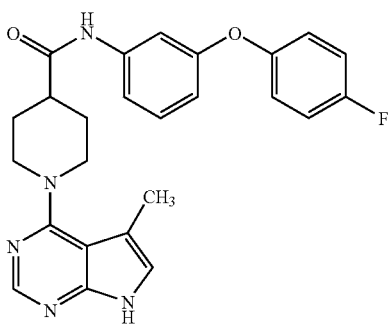

A. Preparation of 4-chloro-5-methyl-7H-pyrrolo[2,3-d]pyrimidine 4-chloro-5-methyl-7H-pyrrolo[2,3-d]pyrimidine was synthesized using procedures outlined in *J. Org. Chem.* 26:4959 (1961) and the references therein.

B. Preparation of 3-(4-fluoro-phenoxy)-phenylamine

In a dry microwave vessel with stir bar, 3-bromoaniline (316 μL, 0.029 mol) and 4-flourophenol (716 mg, 0.064 mol) were added to anhydrous pyridine (10 mL) under nitrogen. To this was added potassium carbonate (1.6 g, 120 mol) and copper(II) oxide (1.2 g, 145 mol). The microwave vessel was sealed then heated in the microwave at normal absorbance at 210° C. for 40 min. The cooled reaction was filtered through a bed of Celite with ethyl acetate. The filtrate was then washed 3 times with concentrated aqueous NaHSO$_4$ and twice with concentrated aqueous NaCl. The organic layer was then dried over magnesium sulfate, filtered and concentrated. Purification over silica using an eluent of hexane and ethyl acetate with a gradient of 0-23% ethyl acetate over 45 min gave 3-(4-fluoro-phenoxy)-phenylamine.

Alternatively, 3-(4-fluoro-phenoxy)-phenylamine was prepared by a two-step procedure by heating a suspension of m-fluoronitrobenzene (4.06 g, 28.7 mmol), p-fluorophenol (3.21 g, 28.6 mmol) and K$_2$CO$_3$ (8.13 g, 58.8 mmol) in DMA (dimethylamine) (60 mL) at 150° C. for 3 hours. The brown reaction mixture was concentrated to one-quarter original volume, diluted with ethyl acetate (220 mL) and washed successively with water (220 mL), 1N NaOH (220 mL) and brine (220 mL). The organic layer was dried (MgSO$_4$) and the solvent removed in vacuo to afford the diphenylether (5.30 g, 80%) as a brown oil.

The crude oil (11.7 g, 0.50 mol) was added to a mixture of 10% Pd/C (1.1 g) in ethyl acetate (5 mL) in a Parr reaction vessel. The reaction was further diluted with ethyl acetate (100 mL). The mixture was then shaken in an hydrogenator at 50 psi for 5 hours and then filtered through Celite. The filtrate was concentrated to give a brown oil (8.7 g, 86%) which was used crude in subsequent steps.

C. Preparation of 4-[3-(4-fluoro-phenoxy)-phenyl-carbamoyl]-piperidine-1-carboxylic acid tert-butyl ester To a mixture of N-Boc piperidine-4-carboxylic acid (9.2 g, 0.04 mol) and DCC (dicyclohexylcarbodiimide) (8.2 g, 0.04 mol) in ethyl acetate (150 mL) was added HOAt (1-hydroxy-7-azabenzotriazole) (5.5 g, 0.04 mol) in DMF (dimethylformamide) (40 mL). The mixture was stirred at room temperature for 10 minutes and then 3-(4-fluoro-phenoxy)-phenylamine (8.7 g, 0.043 mol) in ethyl acetate (50 mL) was added. The reaction mixture was allowed to stir overnight at room temperature and then was concentrated to remove most of the ethyl acetate. The precipitated solid was removed by filtration through Celite. The filtrate was diluted with ethyl acetate and washed with 1 N HCl, saturated NaHCO$_3$ and brine (3×60 mL). The organic phase was dried with MgSO$_4$ and concentrated. The residue was purified on silica eluting with 20% ethyl acetate/hexanes to afford 4-[3-(4-fluoro-phenoxy)-phenylcarbamoyl]-piperidine-1-carboxylic acid tert-butyl ester (14.2 g, 86%) as an off-white solid.

D. Preparation of piperidine-4-carboxylic acid [3-(4-fluoro-phenoxy)-phenyl]-amide hydrochloride 4-[3-(4-fluoro-phenoxy)-phenylcarbamoyl]-piperidine-1-carboxylic acid tert-butyl ester (15 g, 0.036 mol) was dissolved in 4 N HCl in dioxane (160 mL) and stirred overnight at room temperature. The volume of the reaction was reduced to remove most of the dioxane and the residue was filtered to afford piperidine-4-carboxylic acid [3-(4-fluoro-phenoxy)-phenyl]-amide hydrochloride (11.7 g, 96%) as a white solid.

E. Preparation of 1-(5-methyl-7H-pyrrolo[2,3-d]pyrimidin-4-yl)-piperidine-4-carboxylic acid [3-(4-fluoro-phenoxy)-phenyl]-amide A mixture of piperidine-4-carboxylic acid [3-(4-fluoro-phenoxy)-phenyl]-amide hydrochloride (2.51 g, 7.16 mmol) and 4-chloro-5-methyl-7H-pyrrolo[2,3-d]pyrimidine (1.00 g, 5.97 mmol) in iso-propanol (15 mL) was placed in a microwave vessel, followed by addition of triethylamine (2.5 mL, 18 mmol). The microwave vessel was sealed then heated in the microwave at normal absorbance at 190° C. for 60 min. The mixture was concentrated to remove most of the iso-propanol and triethylamine. The residue was washed with methanol (2×15 mL) to afford a brown solid. The solid was washed with water (3×30 mL) and dried overnight to afford 1-(5-methyl-7H-pyrrolo[2,3-d]pyrimidin-4-yl)-piperidine-4-carboxylic acid [3-(4-fluoro-phenoxy)-phenyl]-amide (1.83 g, 69%) as a light-brown solid ((M+H)+: 446.3).

5.2. Preparation of [3-(4-Fluoro-phenoxy)-phenyl]-[1-(5-methyl-7H-Pyrrolo[2,3-d]-pyrimidin-4-yl)-piperidin-4-ylmethyl]-amine

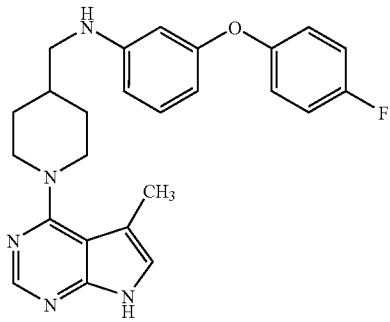

A solution of 1-(5-methyl-7H-pyrrolo[2,3-d]pyrimidin-4-yl)-piperidine-4-carboxylic acid [3-(4-fluoro-phenoxy)-phenyl]-amide (52 mg, 0.12 mmol) in anhydrous THF (tetrahydrofuran) (10 mL) was cooled in an ice bath for 15 minutes with stirring. To this a solution of LAH (lithium aluminum hydride) in THF (1.0 M, 1.2 mL, 1.2 mmol) was added slowly. The reaction mixture was warmed to room temperature and stirred for 15 minutes, and then heated to reflux for 2 hours. The mixture was cooled to room temperature and then $Na_2SO_4 \cdot 10H_2O$ was added until bubbling stopped. After stirring for 2 hours, the precipitate was filtered off and the filtrate concentrated. The residue was dissolved in acetonitrile (1.5 mL) and 30% aqueous TFA (trifluoroacetic acid) (0.5 mL), filtered, and chromatographed using reverse-phase high-pressure liquid chromatography. The clean fractions were pooled and concentrated and then lyophilized to remove water to yield [3-(4-fluoro-phenoxy)-phenyl]-[1-(5-methyl-7H-pyrrolo[2,3-d]pyrimidin-4-yl)-piperidin-4-ylmethyl]-amine as a white solid (7.9 mg, 15%, (M+H)+:432).

5.3. Preparation of 1-(5-Chloro-7H-pyrrolo[2,3-d]pyrimidin-4-yl)-piperidine-4-carboxylic acid [3-(4-fluoro-phenoxy)-phenyl]-amide

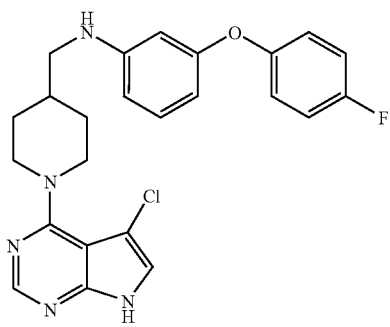

A. Preparation of 4,5-dichloro-7H-pyrrolo[2,3-d]pyrimidine

Following the procedure in Pdulo, J. S.; Saxena, N. K.; Nassiri, M. R.; Turk, S. R.; Drach, J. C.; Townsend, L. B. *J. Med. Chem.* 31:2086 (1988), 4-chloro-5-methyl-7H-pyrrolo[2,3-d]pyrimidine (Example 1A, 20. g, 0.13 mol) was suspended in anhydrous dichloromethane (500 mL), followed by addition of N-chlorosuccinimide (20.8 g, 0.160 mol). The reaction mixture was refluxed at 43° C. for 8 hours. The reaction was cooled down, and the white solid was filtered, washed with dichloromethane (300 mL), and dried to give 4,5-dichloro-7H-pyrrolo[2,3-d]pyrimidine (20 g, 83%)

B. Preparation of [3-(4-Fluoro-phenoxy)-phenyl]-piperidin-4-ylmethyl-amine

A heavy-walled glass tube was charged with piperidine-4-carboxylic acid [3-(4-fluoro-phenoxy)-phenyl]-amide hydrochloride (Example 1D, 5.1 g, 0.016 mol) in dry THF (20 mL) followed by addition of $BH_3$ (1 M in THF, 48 mL) at room temperature. The tube was sealed and then heated at 65° C. for 20 hours. The resulting reaction mixture was cooled to room temperature, evaporated to dryness, and quenched by the addition of 1 N HCl (5 mL) with stirring for 2 hours. The pH was then adjusted to pH 8 with 1 N ammonium hydroxide and the product was extracted with ethyl acetate (100 mL×2), dried over $MgSO_4$, and concentrated to give an off-white solid (4.5 g, 93%).

C. Preparation of [3-(4-Fluoro-phenoxy)-phenyl]-[1-(5-chloro-7H-pyrrolo[2,3-d]-pyrimidin-4-yl)-piperidin-4-ylmethyl]-amine dihydrochloride salt A suspension of [3-(4-Fluoro-phenoxy)-phenyl]-piperidin-4-ylmethyl-amine (4.5 g, 0.015 mol) and 4,5-dichloro-7H-pyrrolo[2,3-d]pyrimidine (2.82 g, 0.015 mol) in i-PrOH (300 mL) was placed in a round-bottomed flask. Following addition of triethylamine (3 g, 0.030 mol), the reaction mixture was then heated at 85° C. for 22 hours with stirring. The whole solution became clear after half an hour. After the reaction was complete as determined by LC/MS, the resulting mixture was allowed to cool to room temperature.

The precipitated solid was isolated from the reaction mixture by filtration on a Büchner funnel and washed with water (10 mL) and then cold methanol (10 mL), dried under vacuum overnight to provide [3-(4-Fluoro-phenoxy)-phenyl]-[1-(5-chloro-7H-pyrrolo[2,3-d]-pyrimidin-4-yl)-piperidin-4-ylmethyl]-amine (4.5 g, 66%). The mother liqueur was allowed to stand overnight, an additional amount of product was isolated (0.6 g, 76%). The solid was suspended in 1 N HCl (20 mL) and strried at room temperature for an hour. The solid product was filtered and washed with ice-water (10 mL) and then cold methanol (10 ml). The isolated solid was dried in a vacuum at 60° C. overnight to give [3-(4-Fluoro-phenoxy)-phenyl]-[1-(5-chloro-7H-pyrrolo[2,3-d]-pyrimidin-4-yl)-piperidin-4-ylmethyl]-amine dihydrochloride salt (4.62 g 78%) as a tan solid. ((M+H)+: 452.0).

5.4. Additional Compounds

The following additional compounds were prepared using methods described herein and methods known in the art:

TABLE 1

| Compound No. | Structure | Formula | MS (M + H)+ |
|---|---|---|---|
| 4 | 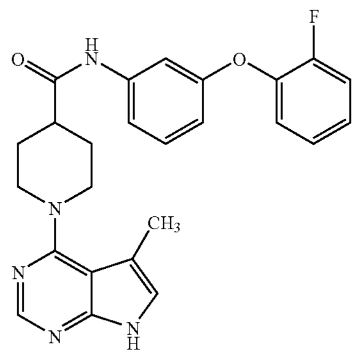 | $C_{25}H_{24}FN_5O_2$ | 446 |
| 5 | 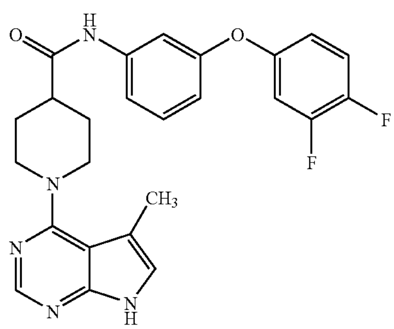 | $C_{25}H_{23}F_2N_5O_2$ | 464 |
| 6 | 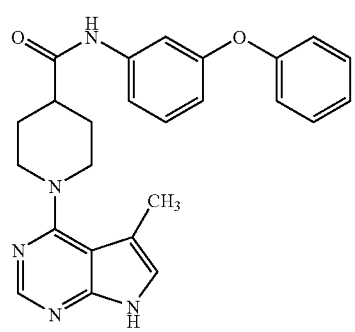 | $C_{25}H_{25}N_5O_2$ | 427.9 |
| 7 | 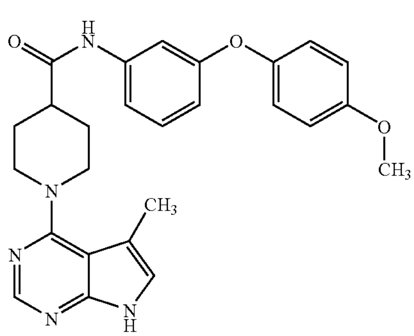 | $C_{26}H_{27}N_5O_3$ | 458 |

TABLE 1-continued

| Compound No. | Structure | Formula | MS (M + H)+ |
|---|---|---|---|
| 8 | 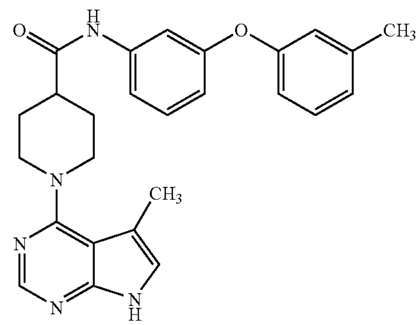 | C₂₆H₂₇N₅O₂ | 442 |
| 9 | 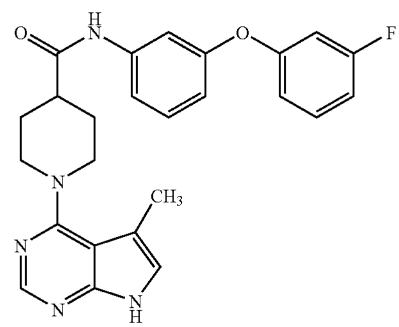 | C₂₅H₂₄FN₅O₂ | 446 |
| 10 | 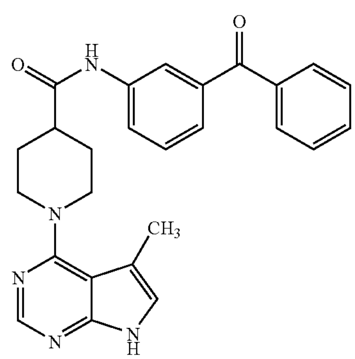 | C₂₆H₂₅N₅O₂ | 440.4 |
| 11 | 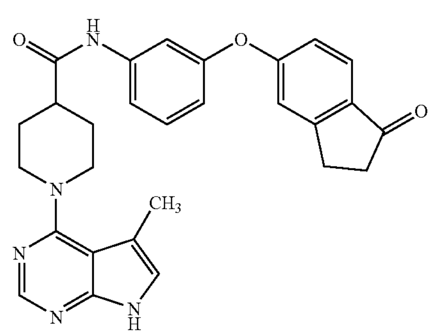 | C₂₈H₂₇N₅O₃ | 484.6 |

TABLE 1-continued
| Compound No. | Structure | Formula | MS (M + H)+ |
|---|---|---|---|
| 12 | 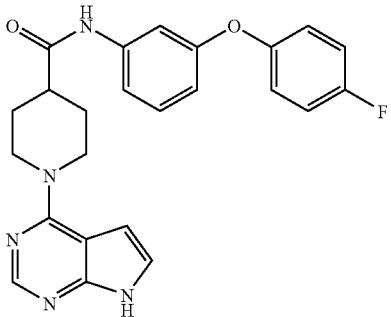 | C$_{24}$H$_{22}$FN$_5$O$_2$ | 432 |
| 13 | 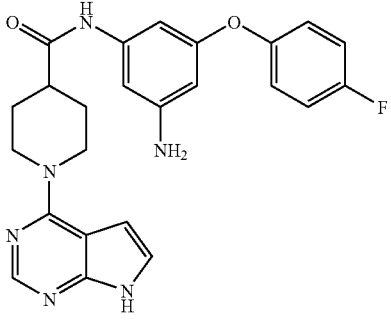 | C$_{24}$H$_{23}$FN$_6$O$_2$ | 447 |
| 14 | 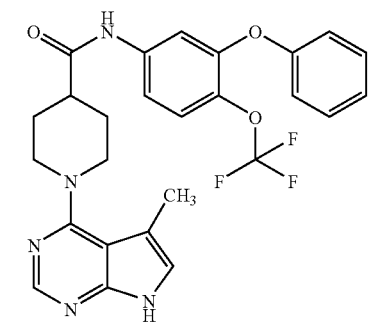 | C$_{26}$H$_{24}$F$_3$N$_5$O$_3$ | 511 |
| 15 | 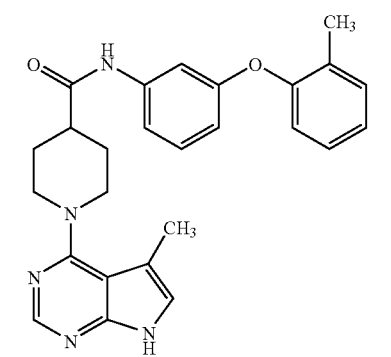 | C$_{26}$H$_{27}$N$_5$O$_2$ | 442 |

TABLE 1-continued

| Compound No. | Structure | Formula | MS (M + H)+ |
|---|---|---|---|
| 16 | 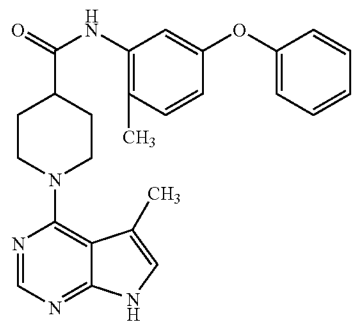 | $C_{26}H_{27}N_5O_2$ | 442 |
| 17 | 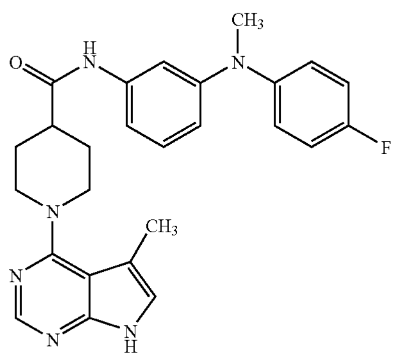 | $C_{26}H_{27}FN_6O$ | 459.5 |
| 18 | 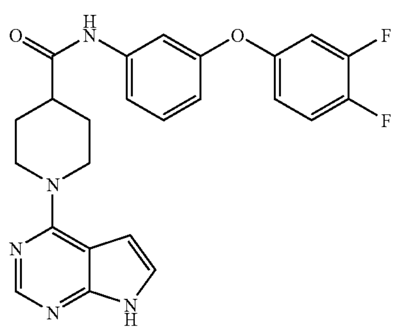 | $C_{24}H_{21}F_2N_5O_2$ | 450 |
| 19 | 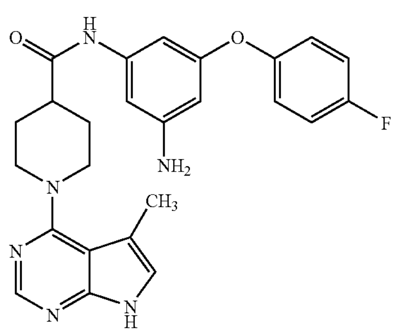 | $C_{25}H_{25}FN_6O_2$ | 461 |

TABLE 1-continued

| Compound No. | Structure | Formula | MS (M + H)+ |
|---|---|---|---|
| 20 | 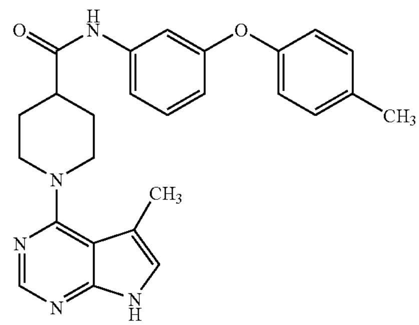 | $C_{26}H_{27}N_5O_2$ | 442 |
| 21 | 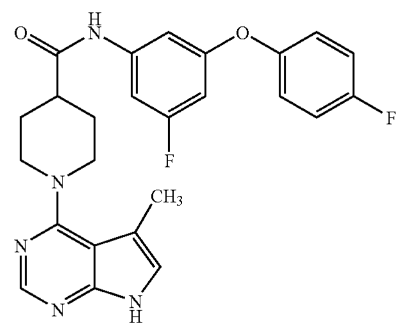 | $C_{25}H_{23}F_2N_5O_2$ | 464 |
| 22 | 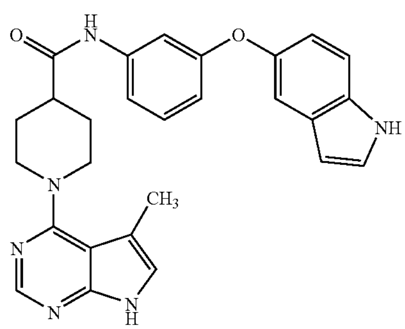 | $C_{27}H_{26}N_6O_2$ | 467 |
| 23 | 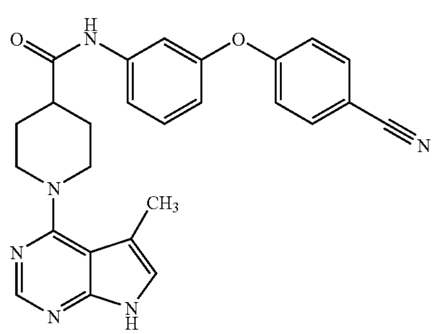 | $C_{26}H_{24}N_6O_2$ | 453 |

TABLE 1-continued

| Compound No. | Structure | Formula | MS (M + H)+ |
|---|---|---|---|
| 24 | 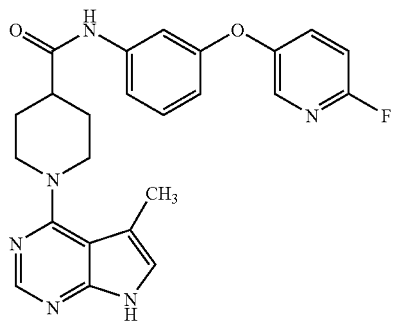 | C24H23FN6O2 | 447 |
| 25 | 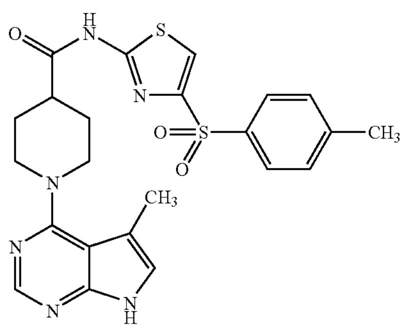 | C23H24N6O3S2 | 497.3 |
| 26 | 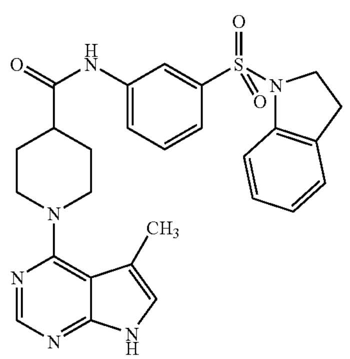 | C27H28N6O3S | 517.4 |
| 27 | 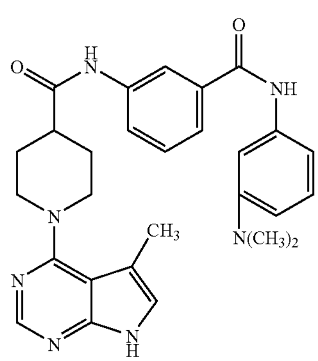 | C28H31N7O2 | 498.2 |

TABLE 1-continued
| Compound No. | Structure | Formula | MS (M + H)+ |
|---|---|---|---|
| 28 | 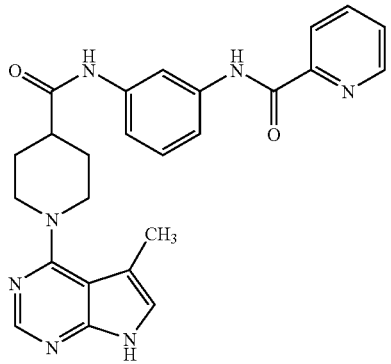 | C25H25N7O2 | 456.3 |
| 29 | 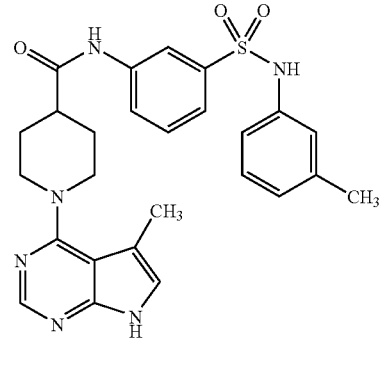 | C26H28N6O3S | 505.4 |
| 30 | 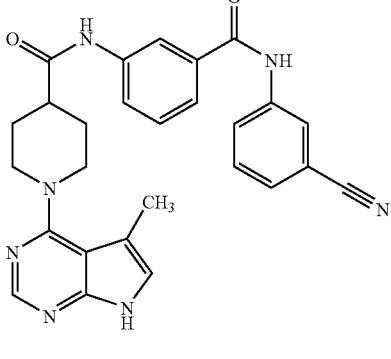 | C27H25N7O2 | 480 |
| 31 | 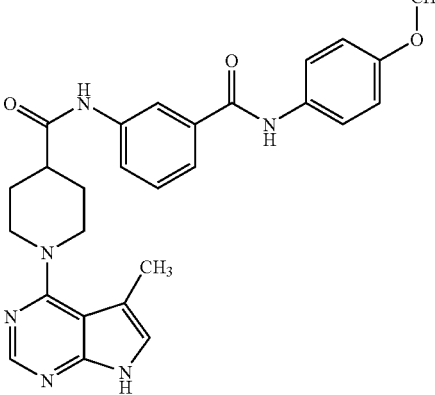 | C27H28N6O3 | 485.5 |

TABLE 1-continued
| Compound No. | Structure | Formula | MS (M + H)+ |
|---|---|---|---|
| 32 | 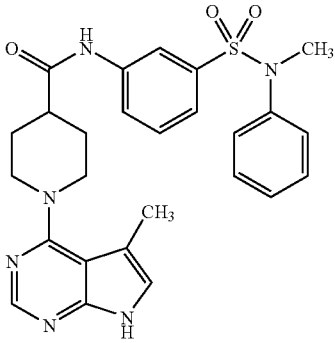 | C26H28N6O3S | 505.1 |
| 33 | 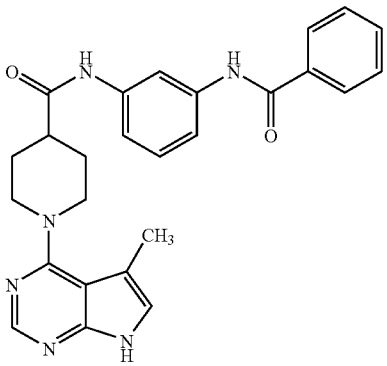 | C26H26N6O2 | 455.4 |
| 34 | 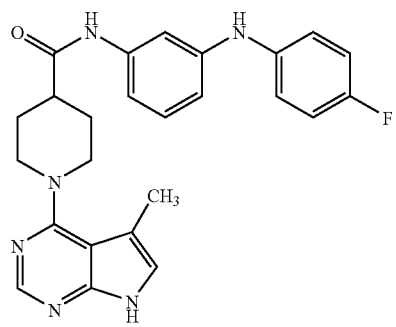 | C25H25FN6O | 446 |
| 35 | 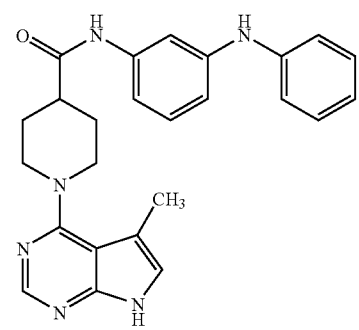 | C25H26N6O | 427.3 |

TABLE 1-continued
| Compound No. | Structure | Formula | MS (M + H)+ |
|---|---|---|---|
| 36 | 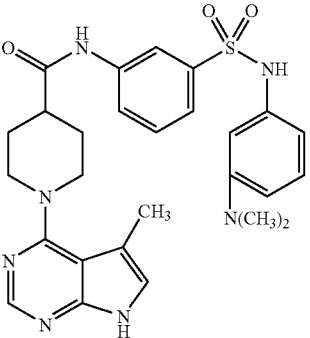 | $C_{27}H_{31}N_7O_3S$ | 534.2 |
| 37 | 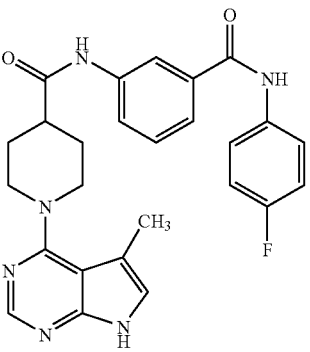 | $C_{26}H_{25}FN_6O_2$ | 473 |
| 38 | 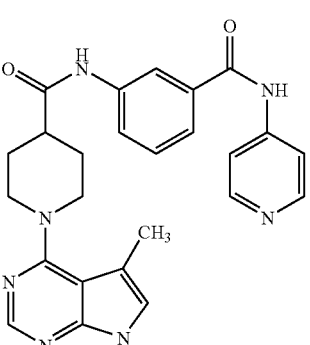 | $C_{25}H_{25}N_7O_2$ | 456 |
| 39 | 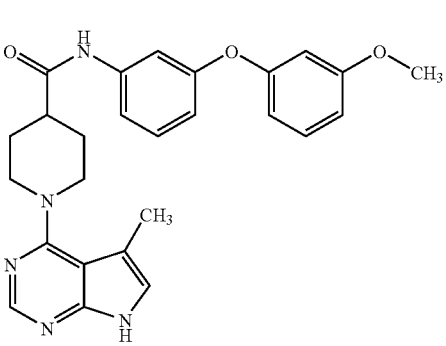 | $C_{26}H_{27}N_5O_3$ | 458 |

TABLE 1-continued
| Compound No. | Structure | Formula | MS (M + H)+ |
|---|---|---|---|
| 40 | 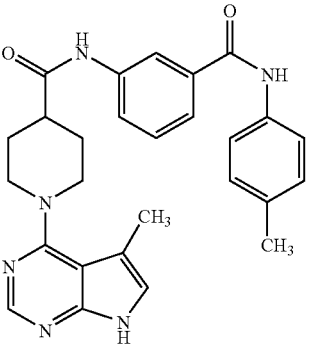 | $C_{27}H_{28}N_6O_2$ | 469 |
| 41 | 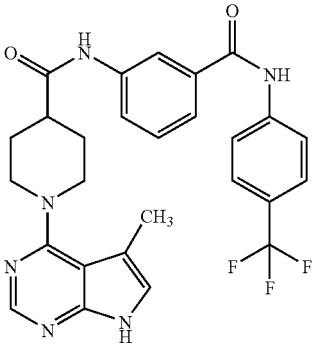 | $C_{27}H_{25}F_3N_6O_2$ | 523 |
| 42 | 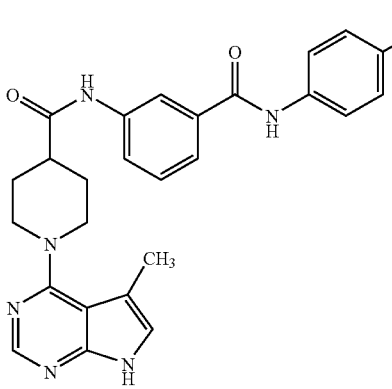 | $C_{27}H_{25}N_7O_2$ | 480 |
| 43 | 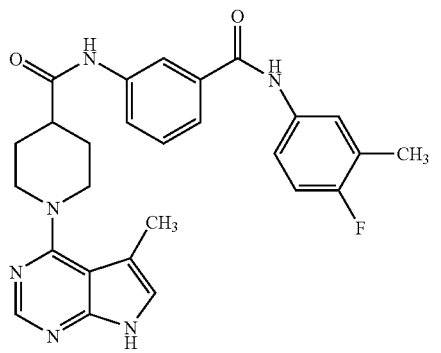 | $C_{27}H_{27}FN_6O_2$ | 487 |

TABLE 1-continued
| Compound No. | Structure | Formula | MS (M + H)+ |
|---|---|---|---|
| 44 | 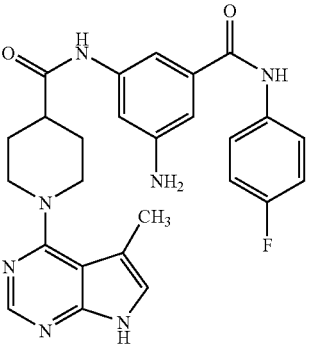 | C26H26FN7O2 | 488.4 |
| 45 | 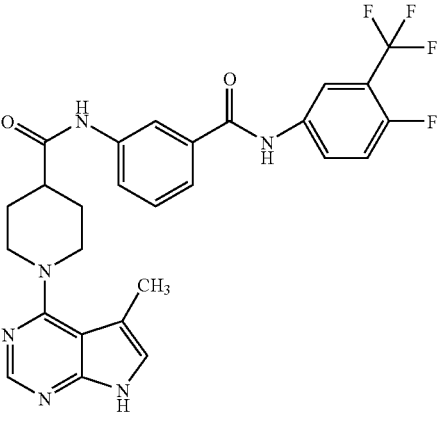 | C27H24F4N6O2 | 541 |
| 46 | 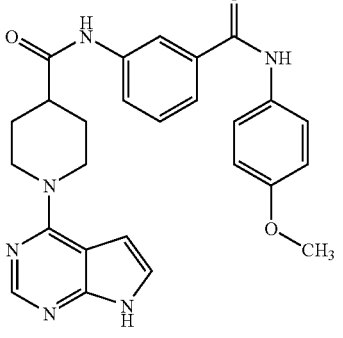 | C26H26N6O3 | 471 |
| 47 | 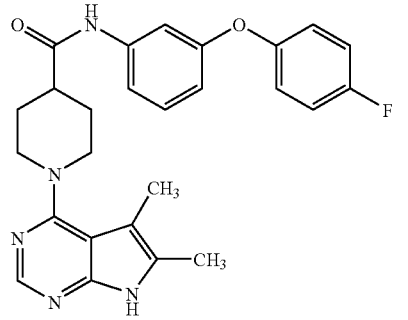 | C26H26FN5O2 | 460 |

TABLE 1-continued
| Compound No. | Structure | Formula | MS (M + H)+ |
|---|---|---|---|
| 48 | 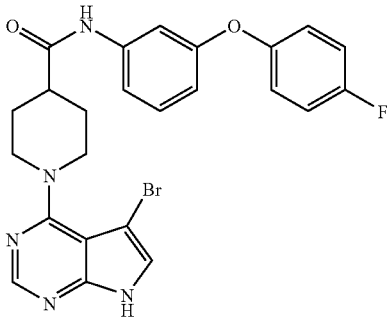 | C24H21BrFN5O2 | 512 |
| 49 | 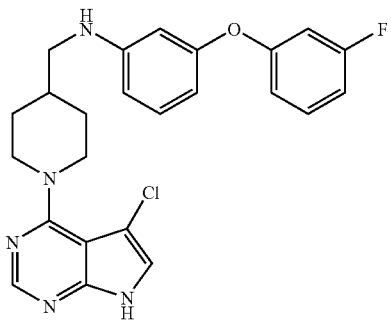 | C24H23ClFN5O | 452 |
| 50 | 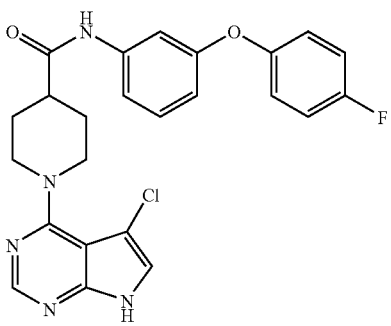 | C24H21ClFN5O2 | 466.1 |
| 51 | 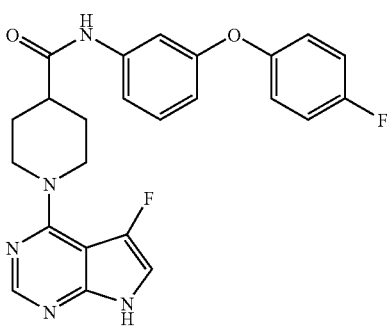 | C24H21F2N5O2 | 450 |

TABLE 1-continued
| Compound No. | Structure | Formula | MS (M + H)+ |
|---|---|---|---|
| 52 | 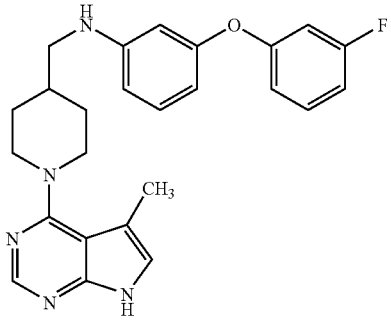 | C25H26FN5O | 432 |
| 53 | 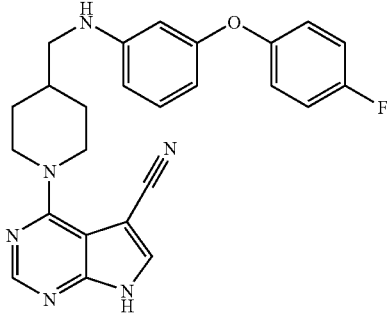 | C25H23FN6O | 433.1 |
| 54 | 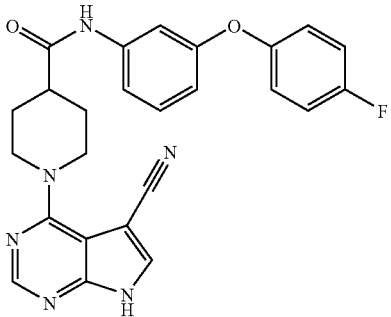 | C25H21FN6O2 | 457 |
| 55 | 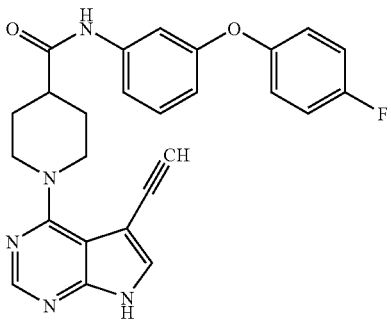 | C26H22FN5O2 | 456 |

TABLE 1-continued

| Compound No. | Structure | Formula | MS (M + H)+ |
|---|---|---|---|
| 56 | 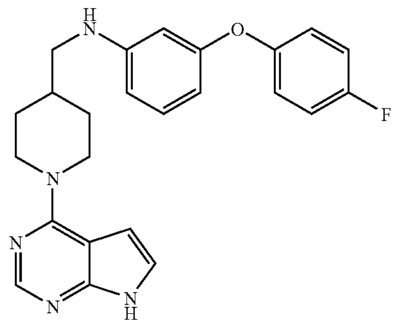 | $C_{24}H_{24}FN_5O$ | 418 |
| 57 | 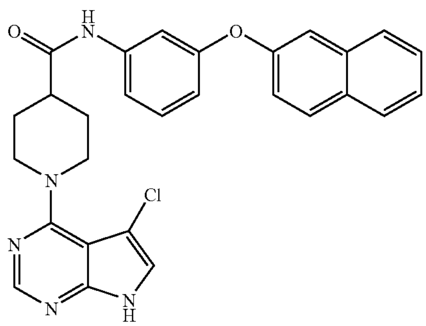 | $C_{28}H_{24}ClN_5O_2$ | 499.7 |
| 58 | 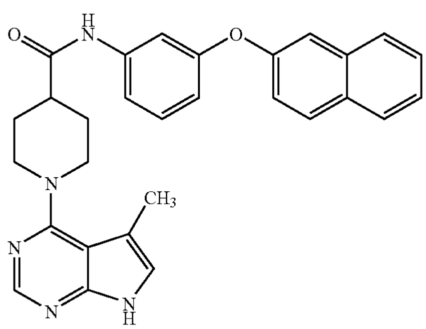 | $C_{29}H_{27}N_5O_2$ | 478.0 |

5.5. Anti-Proliferative Assay

The cytotoxicity of compounds of the invention was tested using cell-based assays performed in 96-well plates using different human tumor cell lines. These human tumor cell lines were purchased from either ATCC (American Type Culture Collection) or NCI (National Cancer Institute) and cultured in RPMI1640 medium with 10% FCS (fetal calf serum). When confluent, the cells were trypsinized, washed with the growth medium, and counted. $6.0 \times 10^3$ cells (200 µl) were seeded into each well of a 96-well culture plate and the cells were cultured overnight. For each cell line, three entire rows of 6 wells for each test compound were used. One row with media alone (no cells) serves as blanks. An individual plate is required for 0 hour and 72 hours assessment of cell proliferation after adding different concentrations of test compounds or positive control or negative control compounds. Compounds were dissolved in DMSO (dimethyl sulfoxide) and serially diluted to a final concentration range of 0.1-30 µM in 5% DMSO. The cells were then incubated at 37° C. in a humidified 5% $CO_2$ atmosphere for 72 hours. Then, 100 µl of the culture medium was carefully removed from each well of the 96-well plates using a multi-channel pipettor. Twenty µl of pre-warmed MTS reagent (Promega, cat. G3580) was added to each well (including the "blank" wells with no cells), mixed carefully by tapping the plate, and immediately placed in a 37° C., $CO_2$ incubator. After one hour of incubation, the plates were removed from the incubator, taped gently to ensure solubilization and even dispersion of the colored reaction product, and the absorbance at 490 nm was determined using a plate reader. The data were statistically analyzed.

The specific compounds disclosed above were subjected to the anti-proliferative assay and determined to have sufficient cytostatic and/or cytotoxic activity.

Other embodiments of the invention will be apparent to those skilled in the art from consideration of the specification and practice of the invention disclosed herein. All cited publications and patents are herein incorporated by reference in their entireties.

What is claimed is:

1. A compound of the formula:

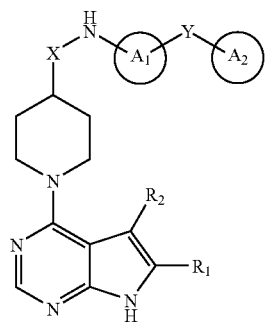

or a pharmaceutically acceptable salt thereof, wherein:
- $A_1$ and $A_2$ are each independently optionally substituted aryl or heteroaryl;
- X is —$CH_2$— or —C(O)—;
- Y is —O—, —$NR_5$—, —$S(O)_nNR_5$—, —$C(O)NR_5$—, —$NR_5C(O)$—, —C(O)—, or —$S(O)_n$—;
- n is 1 or 2;
- $R_1$ and $R_2$ are each independently hydrogen, halo, cyano, hydroxy, —$NR_3R_4$, [thio,] or optionally substituted alkyl, alkoxy, aryl, arylalkyl, heterocycle or heterocycloalkylalkyl; and
- $R_3$, $R_4$, and $R_5$ are each independently hydrogen or optionally substituted alkyl, aryl, arylalkyl, heterocycle or heterocycloalkylalkyl.

2. The compound of claim 1, wherein $R_2$ is hydrogen, cyano, methyl or halo.

3. The compound of claim 1, wherein $R_3$ is hydrogen or alkyl.

4. The compound of claim 1, wherein $R_4$ is hydrogen or alkyl.

5. The compound of claim 1, wherein $R_5$ is hydrogen or lower alkyl.

6. A compound of the formula:

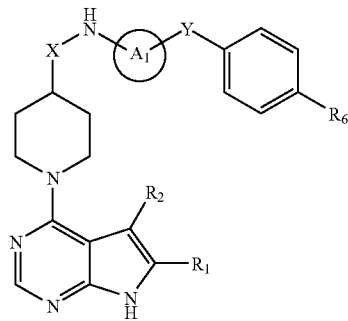

or a pharmaceutically acceptable salt thereof, wherein:
- $A_1$ is optionally substituted aryl or heteroaryl;
- X is —$CH_2$— or —C(O)—;
- Y is —O—, —$NR_5$—, —$S(O)_nNR_5$—, —$C(O)NR_5$—, —$NR_5C(O)$—, —C(O)—, or —$S(O)_n$—;
- n is 1 or 2;
- $R_1$ and $R_2$ are each independently hydrogen, halo, cyano, hydroxy, —$NR_3R_4$, [thio,] or optionally substituted alkyl, alkoxy, aryl, arylalkyl, heterocycle or heterocycloalkylalkyl;
- $R_3$, $R_4$, and $R_5$ are each independently hydrogen or optionally substituted alkyl, aryl, arylalkyl, heterocycle or heterocycloalkylalkyl; and
- $R_6$ is hydrogen, halo, cyano, hydroxy, alkoxy, amino or optionally substituted alkyl.

7. The compound of claim 6, wherein $A_1$ is thiazolyl or optionally substituted phenyl.

8. The compound of claim 6, wherein Y is —O—, —C(O)—, —NHC(O)— or —C(O)NH—.

9. The compound of claim 6, wherein Y is —$S(O)_nNR_5$— or —$S(O)_n$—, and n is 2.

10. The compound of claim 6, wherein $R_1$ is hydrogen.

11. The compound of claim 6, wherein $R_2$ is hydrogen, cyano, methyl or halo.

12. A compound of the formula:

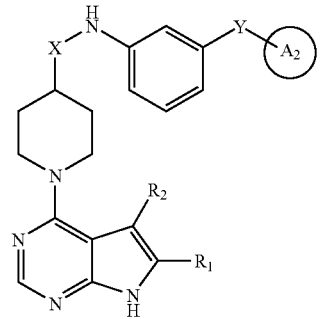

or a pharmaceutically acceptable salt thereof, wherein:
- $A_2$ is optionally substituted aryl or heteroaryl;
- X is —$CH_2$— or —C(O)—;
- Y is —O—, —$NR_5$—, —$S(O)_nNR_5$—, —$C(O)NR_5$—, —$NR_5C(O)$—, —C(O)—, or —$S(O)_n$—;
- n is 1 or 2;
- $R_1$ and $R_2$ are each independently hydrogen, halo, cyano, hydroxy, —$NR_3R_4$, [thio,] or optionally substituted alkyl, alkoxy, aryl, arylalkyl, heterocycle or heterocycloalkylalkyl; and
- $R_3$, $R_4$, and $R_5$ are each independently hydrogen or optionally substituted alkyl, aryl, arylalkyl, heterocycle or heterocycloalkylalkyl.

13. The compound of claim 12, wherein $A_2$ is optionally substituted phenyl, indanyl, indenyl, indolinyl, or pyridyl.

14. The compound of claim 12, wherein Y is —O—, —C(O)—, —NHC(O)— or —C(O)NH—.

15. The compound of claim 12, wherein Y is —$S(O)_nNR_5$— or —$S(O)_n$—, and n is 2.

16. The compound of claim 12, wherein $R_1$ is hydrogen.

17. The compound of claim 12, wherein $R_2$ is hydrogen, cyano, methyl or halo.

18. A composition comprising a compound of claim 1 and a solvent.

* * * * *